United States Patent [19]

Umemoto et al.

[11] Patent Number: 4,631,342
[45] Date of Patent: Dec. 23, 1986

[54] PROCESS FOR PRODUCING 5-FLUOROURACIL

[75] Inventors: Teruo Umemoto, Kanagawa; Eiji Ogura, Tokyo, both of Japan

[73] Assignees: Onoda Cement Company, Ltd., Yamaguchi; Sagami Chemical Research Center, Tokyo, both of Japan

[21] Appl. No.: 709,284

[22] Filed: Mar. 7, 1985

[30] Foreign Application Priority Data

Mar. 9, 1984 [JP] Japan ................... 59-43779

[51] Int. Cl.$^4$ ............................ C07D 239/22
[52] U.S. Cl. .................... 544/313; 260/694
[58] Field of Search ............ 544/313; 260/694

[56] References Cited

U.S. PATENT DOCUMENTS

| 3,682,917 | 8/1972 | Knuniants et al. | 544/313 |
| 3,846,429 | 11/1974 | Giller et al. | 544/313 |
| 3,954,758 | 5/1976 | Schuman et al. | 544/313 |
| 4,029,661 | 6/1977 | Schuman et al. | 544/313 |
| 4,082,752 | 4/1978 | Takahara et al. | 544/313 |
| 4,524,032 | 6/1985 | Misaki et al. | 260/694 |

FOREIGN PATENT DOCUMENTS

| 50-25476 | 8/1975 | Japan . | |
| 51-149287 | 12/1976 | Japan . | |
| 52-133994 | 11/1977 | Japan . | |
| 0059681 | 5/1978 | Japan | 544/313 |
| 55-81818 | 6/1980 | Japan . | |
| 59-16880 | 1/1984 | Japan . | |
| 0144767 | 8/1984 | Japan | 544/313 |

Primary Examiner—Donald G. Daus
Assistant Examiner—Stephen M. Kapner
Attorney, Agent, or Firm—Wenderoth, Lind & Ponack

[57] ABSTRACT

A process for producing 5-fluorouracil using an aqueous phosphoric acid solution as a solvent which is a good solvent for an intermediate resulting from the reaction between uracil and elemental fluorine, and permits the reaction to proceed smoothly, but which can precipitate the final product, 5-fluorouracil, after cooling the heat-treated reaction solution to room temperature, with no need to evaporate the solvent.

The process comprises reacting uracil in an aqueous phosphoric acid solution with elemental fluorine and heating the resultant reaction solution to form 5-fluorouracil.

6 Claims, No Drawings

PROCESS FOR PRODUCING 5-FLUOROURACIL

BACKGROUND OF THE INVENTION

The present invention relates to a process for commercially, inexpensively, and also simply producing 5-fluorouracil by a direct fluorination reaction of uracil.

5-fluorouracil, itself is used in large quantities as an anti-tumor and it is also used as a synthetic intermediate for producing other anti-tumors.

Therefore, there is a need for a simple and inexpensive process for producing 5-fluorouracil commercially.

Heretofore, among the processes for producing 5-fluorouracil, a method in which uracil is subjected in a particular medium to a direct fluorination reaction by elemental fluorine has been considered as a relatively advantageous one and thus many processes for improving the direct fluorination of uracil have been proposed. None of these improved process, however, can be said to be satisfactory because of their economics and complexity.

Elemental fluorine has an extremely strong reactivity, i.e. oxidation power, and if uracil is directly exposed to fluorine, ignition or explosion may occur. Thus it is necessary to create a process capable of fluorinating commercially with high economics at the desired position only of uracil, while controlling this violent reaction.

Heretofore, a process in which uracil is reacted in water with elemental fluorine diluted with an inert gas has been used for achieving such a purpose. This process has the decisive drawback that if the process is tried to carry out in good yield in achieving the aimed reaction, a prohibitively low concentration of uracil in water must be employed, thus leading to a lower step efficiency, on the other hand, if better efficiency is aimed at, a polyfluorinated by-product such as 5,5-difluoro-6-hydroxy-6-hydrouracil is produced with the remaining unreacted uracil, thus adversely affecting the product purity, which is one of the most important requirements of a medication. For solving the problem set forth above, a number of processes have been proposed in which, the following solvents are used; (1) acetic acid (Japanese Patent Publication No. 50-25476), (2) trifluoroacetic acid (Japanese Laid Open Patent Application No. 51-149287), (3) an aqueous solution of formic acid (Japanese Laid Open Patent Application No. 55-81818), (4) a concentrated aqueous solution of hydrofluoric acid (Japanese Laid Open Patent Application No. 52-13394), and (5) a mixed solution of hydrogen fluoride and an aliphatic carboxylic acid (Japanese Laid Open Patent Application No. 53-59681).

However, all of these processes are difficult to perform safely on an industrial scale. Acetic acid, formic acid, and an aliphatic carboxylic acid suffer from the drawbacks that they may possibly react with elemental fluorine, thus causing ignition or explosion depending upon the control of the process, and they also are disadvantageous with respect to safety and economics because of the need to use large amounts. On the other hand, hydrogen fluoride and a concentrated aqueous solution of hydrofluoric acid are highly toxic, and their use in large quantities is accompanied by danger.

Trifluoroacetic acid is expensive and thus is economically disadvantageous, even though no danger of explosion exists.

In general, a process for producing 5-fluorouracil starting from uracil and elemental fluorine comprises two steps consisting of a step of reacting uracil with elemental fluorine and a step of thermally treating the resultant intermediate. In the conventional processes, uracil and elemental fluorine is reacted in a particular medium in the first step, and the medium is distilled off from the resultant reaction solution under heating in the second step.

Such distilling off, however, consumes considerable energy. Therefore, an economic and simple process has been desired. In this regard, a process wherein uracil is slurried in a concentrated aqueous solution of hydrosilicofluoric acid and is reacted with elemental fluorine to form a precipitate which is filtered off and the precipitate thus obtained is subjected to high temperature thermal treatment (Japanese Laid Open Patent Application No. 59-16880) offers a prima facie solution of the aforementioned drawbacks.

The process, however, poses the problems that it requires high temperature thermal treatment, that the material for constructing the reaction vessel is limited due to the requirement of resisting highly corrosive hydrosilicofluoric acid, and that cost of the hydrosilicofluoric acid is relatively high.

In addition, due to regulations concerning environmental pollution and waste water the disposal of hydrosilicofluoric acid is a difficult problem. Thus, this method is not truly satisfactory from a commercial viewpoint. Moreover, it is an important matter of public health to cope with the problems stemming from hydrogen fluoride produced as a by-product from a reaction between elemental fluorine and uracil. Heretofore, there has been no means provided for economically solving this problem.

The present inventors have performed numerous studies aimed at solving the following three problems listed below:

(1) selection of a reaction solvent which is commercially available and inexpensive, which is non-inflammable when in contact with elemental fluorine and makes it possible to proceed the fluorination reaction with high efficiency and also which is an absorbent for hydrogen fluoride gas.

(2) the selection of a reaction solvent which has extremely low solubility for the final product, 5-fluorouracil, but an adequate solubility for the intermediate product resulting from the reaction between uracil and elemental fluorine. In other words, a reaction solvent should be selected such that the reaction between uracil and elemental fluorine can proceed smoothly by dissolving the intermediate resulting from said reaction, while allowing the precipitation of the final product, 5-fluorouracil, from the reaction medium after thermal treatment of the intermediate, the precipitation making it possible to effect the separation of the final product, 5-fluorouracil, with ease.

(3) selection of a reaction solvent which has no deleterious effect on the thermal treatment of an intermediate resulting from the reaction between uracil and elemental fluorine and permits the conversion of the intermediate to the final product, 5-fluorouracil, at a relatively low temperature.

As a result of the studies set forth above, the present inventors found that an aqueous phosphoric acid solution satisfies all of the three requirements set forth and were led to the present invention.

SUMMARY OF THE INVENTION

The present invention relates to a process for producing 5-fluorouracil comprising reacting uracil and elemental fluorine in an aqueous phosphoric acid solution and thermally treating the resultant reaction solution to produce effeciently 5-fluorouracil of high purity with high yields.

The aqueous phosphoric acid solution works as an absorbent for the by-product hydrogen fluoride gas resulting from the reaction between the elemental fluorine and uracil, thereby significantly reducing the vapor pressure of the hydrogen fluoride gas. In addition, the aqueous phosphoric acid solution is very inexpensive. For these reasons, the present invention can be said to be especially advantageous for commercial use. The aqueous phosphoric acid solution deposits the 5-fluorouracil as crystals from the reaction system after the thermal treatment of the reaction solution. This makes it easy to separate 5-fluorouracil by means of filtration. The 5-fluorouracil can be purified to high purity by recrystallization from water, for example. These beneficial effects are totally unpredictable based on the prior art.

DETAILED DESCRIPTION OF THE INVENTION

The concentration of the aqueous phosphoric acid solution is preferably between 20 to 100% by weight, and more preferably 50 to 95% by weight, although a weaker or more concentrated solution can be used.

However, if the aqueous phosphoric acid solution is lower in concentration than 20%, the yield of the final product, 5-fluorouracil, is lower and its purity is also reduced.

In order to efficiently produce 5-fluorouracil in accordance with the present invention, preferably 1 to 150 ml and more preferably 2 to 20 ml of the aqueous phosporic acid solution per gram of uracil is employed.

The use of less than 1 ml of the aqueous phosphoric acid solution per gram of uracil does not permit the reaction to proceed efficiently because no slurry formation of uracil occurs. The use of more than 150 ml of the aqueous phosphoric acid per gram of uracil makes the process uneconomical due to an excess of the aqueous phosphoric acid solution.

The reaction between uracil and elemental fluorine may be effected at a temperature between $-30°$ C. and $50°$ C. but it is preferable to carry out the reaction at a temperature between $-10°$ C. and $35°$ C. in order to achieve more efficient production of the final product. If the temperature is lower than $-30°$ C., the reaction rate becomes extremely small, if the reaction temperature is higher than $50°$ C., the formation of a by-product occurs. Thus, both cases result in a reduction in the yield.

In accordance with the present invention, uracil is suspended in the aqueous phosphoric acid solution and is reacted with elemental fluorine under stirring. In order to permit selective fluorination, it is preferable to use the elemental fluorine in admixture with an inert gas to dilute the fluorine. The dilution of the elemental fluorine may be effected, for example, by employing 0 to 200 times by volume of an inert gas such as nitrogen, helium, argon, tetrafluoromethane, sulfur hexafluoride, carbon dioxide, and the like. In order to cause the reaction to proceed more selectively, the concentration of the diluted elemental fluorine may be changed during the process to any concentration desired.

The reaction between the uracil in the aqueous phosphoric acid solution and elemental fluorine may be effected, with regard to the procedure of feeding the elemental fluorine, with either a pass-through method or a batch method. At a lower reaction temperature such as below $0°$ C., it may sometimes become difficult to produce sufficient agitation due to an excessively high viscosity of the slurry comprising uracil in the aqueous phosphoric acid solution. In such a case, it is advisable to significantly reduce the viscosity of the slurry by admixing a solvent in an amount of less than 20% by weight of the solvent with the slurry, the solvent having a lower viscosity than the aqueous phosphoric acid solution and also being miscible with the aqueous phosphoric acid solution such as a nitrile, and an ether, a ketone, an alcohol, a carboxylic acid, and the like. There is no damage to the beneficial properties of the aqueous phosphoric acid solution of the present invention produced by the incorporation of the solvent provided that the amount of the solvent is less than 20% by weight of the solvent of slurry.

As for the quantity of elemental fluorine to be employed relative to the amount of uracil, it is preferable to use at least 1 mole of elemental fluorine for each mole of uracil, and more preferably the molar ratio of elemental fluorine to uracil is 1.0 to 10, much more preferably 1.0 to 4.0, to complete the fluorination reaction. If the molar ratio of elemental fluorine to uracil is less than 1.0, an amount of unreacted uracil will remain, but if the molar ratio is greater than 10, a polyfluorinated by-product will be formed and thus, in either case the purity of 5-fluorouracil will be reduced. In the reaction between uracil and elemental fluorine in the aqueous phosphoric acid solution, the end of the reaction is indicated by the formation of a clear solution from the slurry of uracil in the phosphoric acid. The reaction time required for the completion of the reaction may vary depending upon the reaction temperature, the concentration of elemental fluorine and the concentration of the phosphoric acid in the aqueous phosphoric acid solution and thus it is desirable to select the reaction time by changing the foregoing parameters.

In accordance with the present invention, the reaction solution is heated subsequent to the completion of the fluorination reaction. The temperature to which the reaction solution is heated is in the range of $20°$ C. and $200°$ C. Heating to a temperature within the range of $40°$ C. and $185°$ C. is preferable in order to efficiently effect the reaction and to produce 5-fluorouracil of high purity. Heating to lower than $20°$ C. requires a long period of time for converting the intermediate to 5-fluorouracil. If the heating temperature is higher than $200°$ C., the resultant 5-fluorouracil turns to a remarkably colored material.

After heating, the reaction solution is cooled to room temperature and the resultant precipitated crystals are filtered to obtain raw 5-fluorouracil. The raw product can be purified, for example, through recrystallization from aqueous solution or sublimation, thereby producing highly pure 5-fluorouracil.

As discussed hereinbefore, the present invention can directly solve a number of problems from which the conventional processes suffer.

Next, a number of examples will be given to further illustrate the present invention.

EXAMPLE 1

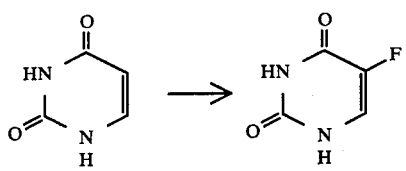

Into a 50 ml flask equipped with a gas blowing inlet was weighed 1.00 gram of uracil to which was added 5 ml of 85% aqueous phosphoric acid solution. Fluorination of uracil was effected by passing through a stream of elemental fluorine diluted to a concentration of 10% with helium which stirring by means of a magnetic stirrer until a clear solution was formed. The temperature of the contents of the flash was kept to 15° C.

After completion of fluorination, the reaction solution was heated to 80° C. and kept at that temperature for one hour. After allowing to cool to room temperature, precipitated crystals were filtered off and the crystals thus obtained were recrystallized using water as the solvent to form 0.81 gram of purified 5-fluorouracil. The yield was 69.0%.

The analysis of the 5-fluorouracil is as follows:
Melting point;
(1) observed 282.0°–282.4° C. (decomposition)
(2) reference 282°–283° C. (decomposition) recited in J. Am. Chem. Soc. 79, 4560 (1957),
$^1$H-NMR (in DMSO-d$_6$, D$_2$O exchange); δ 7.70 (d, J=6.0 Hz)
By high speed liquid chromatography, it was coincident with the reference sample.

EXAMPLE 2

Into a 50 ml Teflon beaker, 1.002 grams of uracil were weighed to which were added 5 ml of an 85% aqueous phosphoric acid solution. The uracil was made into a slurry by stirring with a magnetic stirrer. The Teflon beaker containing the slurry of uracil was placed in a 1 l separable flash (1.4 l of total inner volume) equipped with a gas introducing inlet.

The separable flask was evacuated using a vacuum pump, while it was cooled with ice water. After the evacuation, the fluorination of uracil was carried out by introducing elemental fluorine diluted to 20% concentration with helium into the separable flask until the pressure within the flask reached 0 kg/cm$^2$ gauge and by maintaining the temperature of the flask at 15° C. and stirring the slurry with a magnetic stirrer for 8 hours. After completion of fluorination, the Teflon beaker was removed from the separable flask and it was heat-treated at 100° C. for 1 hour. Thereafter, the beaker was allowed to cool to room temperature and precipitated crystals were filtered off. The crystals thus obtained were recrystallized using water as the solvent to obtain 0.879 gram of 5-fluorouracil with a yield of 75.6%.

EXAMPLE 3

This example was similar to Example 2 except that 10 ml of an 85% aqueous phosphoric acid solution were added to yield 0.785 gram of 5-fluorouracil with a yield of 67.5%.

EXAMPLE 4

This example was carried out as in Example 2 except that 1.003 grams of uracil were used, the reaction temperature was maintained at 0° C., and the reaction was carried out for 24 hours, to yield 0.836 gram of 5-fluorouracil. The yield was 71.8%.

EXAMPLE 5

This example is the same as Example 4 except that 0.998 gram of uracil were used, the reaction temperature was maintained at 20° C., and the reaction continued for 4 hours to yield 0.782 gram of 5-fluorouracil with a yield of 67.5%.

EXAMPLE 6

This example is the same as Example 5, except that 0.999 gram of uracil were used, to which were added 4.5 ml of 90% aqueous phosphoric acid, the reaction temperature was kept to 5° C., and the reaction continued for 8 hours to yield 0.834 gram of 5-fluorouracil with a yield of 71.9%.

EXAMPLE 7

This example is the same as Example 2 except that 1.001 grams of uracil were used, the reaction temperature was maintained at 5° C., and heating was effected for 4 hours to yield 0.946 gram of 5-fluorouracil with a yield of 81.4%.

EXAMPLE 8

This example is the same as Example 7 except that heating was effected for 2 hours to yield 0.936 gram of 5-fluorouracil with a yield of 80.6%.

EXAMPLE 9

This example was carried out as in Example 2 except that 1.000 gram of uracil were used, the reaction temperature was 5° C., and the heat treatment was at 60° C. for 2.5 hours. 0.943 gram of 5-fluorouracil, were obtained with a yield of 81.3%.

EXAMPLE 10

Into a Teflon beaker, 0.999 gram of uracil were weighed to which were added 5 ml of an 85% aqueous phosphoric acid solution to form a slurry. The beaker was placed in a separable flask having a capacity of 1.4 l and after evacuating the flask, elemental fluorine diluted with helium to a concentration of 20% was introduced until the gauge pressure in the flask was 0 kg/cm$^2$. The reaction between uracil and the elemental fluorine was carried out for 8 hours while maintaining the temperature inside the flask at 5° C., followed by heat treatment at 180° C. for 5 minutes.

Thereafter, the contents of the flask were allowed to cool to room temperature. The phosphoric acid solution and precipitated crystals had a deep brown color. After filtering the crystals, the crystals were dissolved in water and the resultant solution was passed through a column of active alumina to remove colorred material.

The aqueous solution thus obtained was completely dried by evaporation and the resultant white crystals were purified by sublimation at 180° C.–200° C. to obtain 0.980 gram of 5-fluorouracil with a yield of 84.5%.

What is claimed is:

1. A process for producing 5-fluorouracil comprising reacting uracil in an aqueous phosphoric acid solution with elemental fluorine and heating the resultant intermediate reaction solution.

2. A process according to claim 1 wherein the reaction between uracil and elemental fluorine is carried out at a temperature between −30° C. to 50° C. and, the heating of the resultant reaction solution is carried out at a temperature between 20° C. to 200° C.

3. A process according to claim 1 wherein said aqueous phosphoric acid solution comprises 20% to 100% by weight of phosphoric acid.

4. A process according to claim 2 wherein said aqueous phosphoric acid solution comprises 20% to 100% by weight of phosphoric acid.

5. A process according to claim 3 wherein the phosphoric acid is present in an amount of 50% to 95% by weight based on the aqueous phosphoric acid solution.

6. A process according to claim 4 wherein the phosphoric acid is present in an amount of 50% to 95% by weight based on the aqueous phosphoric acid solution.

* * * * *